(12) United States Patent
Hsieh

(10) Patent No.: US 8,188,035 B2
(45) Date of Patent: May 29, 2012

(54) METHOD FOR USING NANO CARBON TO REFINE COLLAGEN INTO NANOPARTICULATE COLLAGEN

(76) Inventor: Jen-Too Hsieh, Taipei (TW)

( * ) Notice: Subject to any disclaimer, the term of this patent is extended or adjusted under 35 U.S.C. 154(b) by 477 days.

(21) Appl. No.: 12/453,227

(22) Filed: May 4, 2009

(65) Prior Publication Data

US 2010/0280226 A1    Nov. 4, 2010

(51) Int. Cl.
  *C07K 14/00*    (2006.01)
(52) U.S. Cl. ............................................. 514/2; 977/773

(58) Field of Classification Search .................... None
  See application file for complete search history.

*Primary Examiner* — Anand Desai
(74) *Attorney, Agent, or Firm* — Leong C. Lei

(57) ABSTRACT

This invention relates to a method of using nano carbon to refine collagen into nanoparticulate collagen. As nano carbon particle are mixed into collagen, the pored structure of the nano carbon absorb and adhere to the collagen outer cell membrane and subsequently tears the collagen apart into nanoparticulates via ultrasound vibration, Thus it creates an advanced nanoparticulate collagen small enough to be practically and efficiently absorbed by the skin when applied directly.

1 Claim, 3 Drawing Sheets

A B

C D

METHOD FOR USING NANO CARBON TO REFINE COLLAGEN INTO NANOPARTICULATE COLLAGEN

FIELD OF INVENTION

A method for refining collagen, mainly by using nano carbon as a refining agent coupled with ultrasound vibration to create nanoparticulate collagen.

PRIOR ART OF THE INVENTION

Collagen plays an important role in the maintenance of skin and muscles in the human body. Collagen is protein structure that is approximately 0.5 μm wide made of multiple intertwining protein strands. The dermis layer of human skin takes up approximately 15-20% of total body weight. The dermis consists of approximately 18-30% collagen, thus collagen is an abundant protein in the human body. But without sufficient collagen replenishment the condition of the skin deteriorates over time. It causes wrinkles, sagging, discoloration and other signs of aging of the skin. To reduce the signs of aging, people have been researching various types of skin care products in the hope of achieving an everlasting youthful appearance.

So far, most skin care products' main ingredient is an emulsifying agent mixed with collagen, of which the collagen his traditionally been derived from animal tissues. Using animal collagen sources has its drawbacks, such as contamination from diseases and animal testing. This has spurred the cosmetic industry to use plant based collagen sourced in current generation skin care products. But because plant based collagen molecules are normally larger than that of animals, it becomes even more difficult for the skin to absorb the plant collagen when applied directly. Cosmetic companies often add collagen into their skin care products with claims that it can replenish the collagen in the skin. These claims are questionable at best, mainly because the molecular mass of collagen, at approximately 300,000 Daltons, is too large to penetrate the epidermis layer of the skin. Without further refinement, it is almost impossible for collagen to reach the living skin cells that could benefit most from the collagen. Common collagen refinement methods include breaking collagen molecules under high pressure and speed pulverization. Such methods cause excessive heat, which breaks down the collagen and results in low yields. Other methods include using chemical or microorganisms to break down the collagen or using hydrolysis to refine collagen. These methods also create their own problems. Namely, the maintaining of correct temperatures for collagen preservation and the removal of chemical impurities left behind. Another method for refining collagen as described in Taiwan patent application number 092136774, 'Method for producting Nano-compound collagen', is not focused on creating collagen nanoparticulates but instead taking hydrolyzed collagen, adding silver nanoparticulates, iron nanoparticulates, L-asorbic acid, and other various ingredients to produce cosmetic skin care products. The collagen from this method is gained from animal tissue, which brings into question safety concerns. More importantly, the collagen can only be refined to a molecular mass of 50,000 Daltons, which is still to large for the skin to effectively absorb, thus this method can not create real and practical results.

SUMMARY OF THE INVENTION

The biochemical industry's common recognition is that collagen must be refined to under 3,000 Daltons (or under 30 nano meters) before it can be directly absorbed by the human skin. Our method for refining collagen into nanoparticulates achieves this level of refinement by using nano carbon particles mixed with hydrolyzed collagen. As shown in FIG. 2, when observed under a microscope at a magnification of ×50000, we see the nano carbon particles are approximately 80 nano meters wide and the pored structure is covered with gaps that are approximately 0.8 nano meters wide. These gaps can absorb collagen molecules larger than the gap itself. These countless gaps act like the suction cups of an octopus's legs, the gaps adhere to the outer cell membrane of the larger collagen, thus surrounding it with nano carbon particles. When an ultrasound shock is introduced, the nano carbon particles begin to shake and tear the larger collagen into smaller particles. This refinement process is repeated until the collagen particulates are smaller than a molecular mass of 3,000 Daltons or 30 nano meters. These collagen nanoparticulates are absorbed within the gaps of the nano carbon and saturate the carbon with collagen. After filtering the nano carbon and collagen mixture through a 300-mesh filter, nano carbon particles containing collagen nanoparticulates can be collected.

The major characteristics of this method collagen refinement are the mixing nano carbon particles with collagen to refine the collagen into particles of a smaller molecular mass. Said method creates collagen that can effectively revitalize and rejuvenate the skin.

BRIEF DESCRIPTION OF THE DRAWINGS AND EXHIBITS

DETAILED DESCRIPTION OF THE PREFERRED EMBODIMENT

Figure 1:
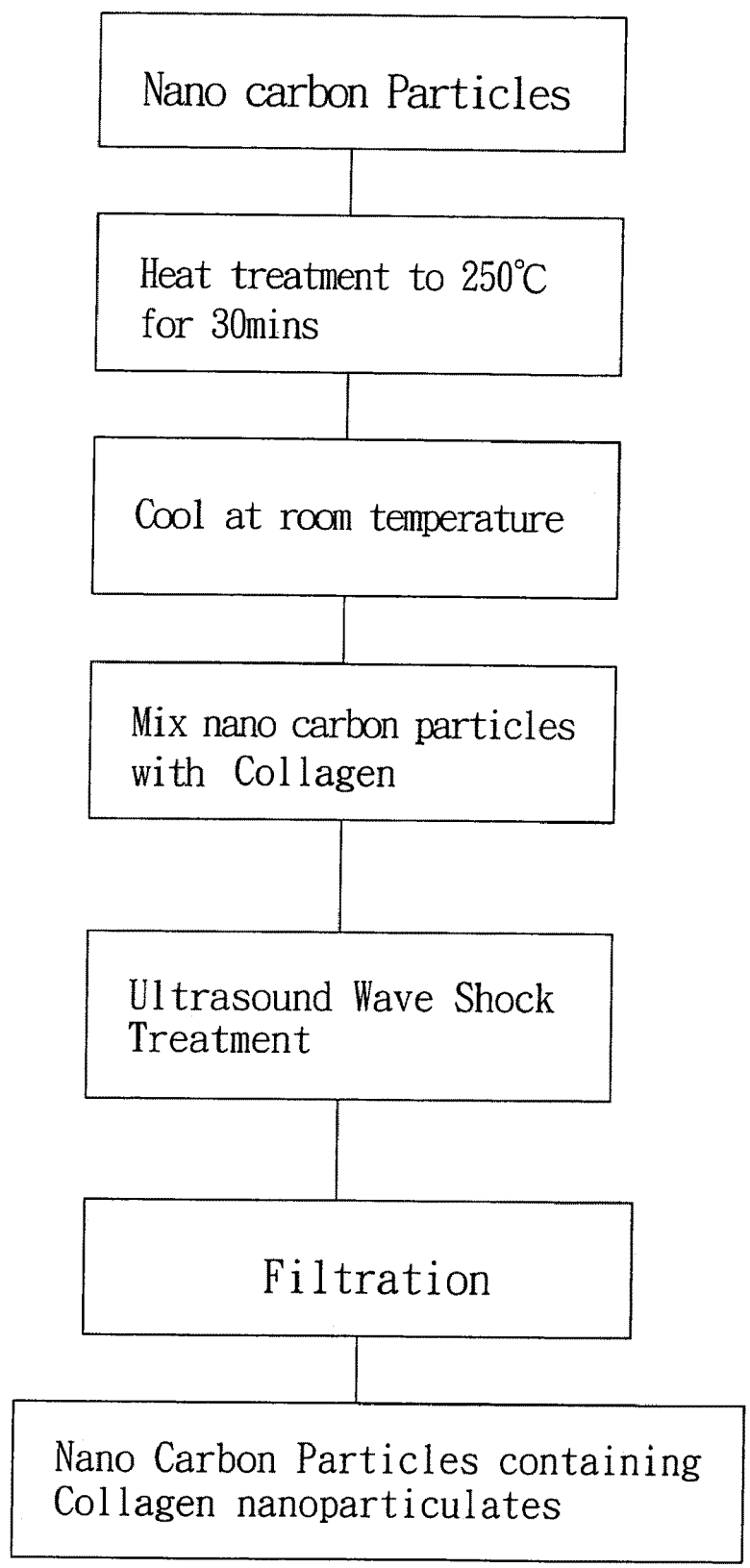
FIG. 1 shows a schematic diagram of the process for preparing collagen nanoparticulates according to the present invention.
Figure 2:
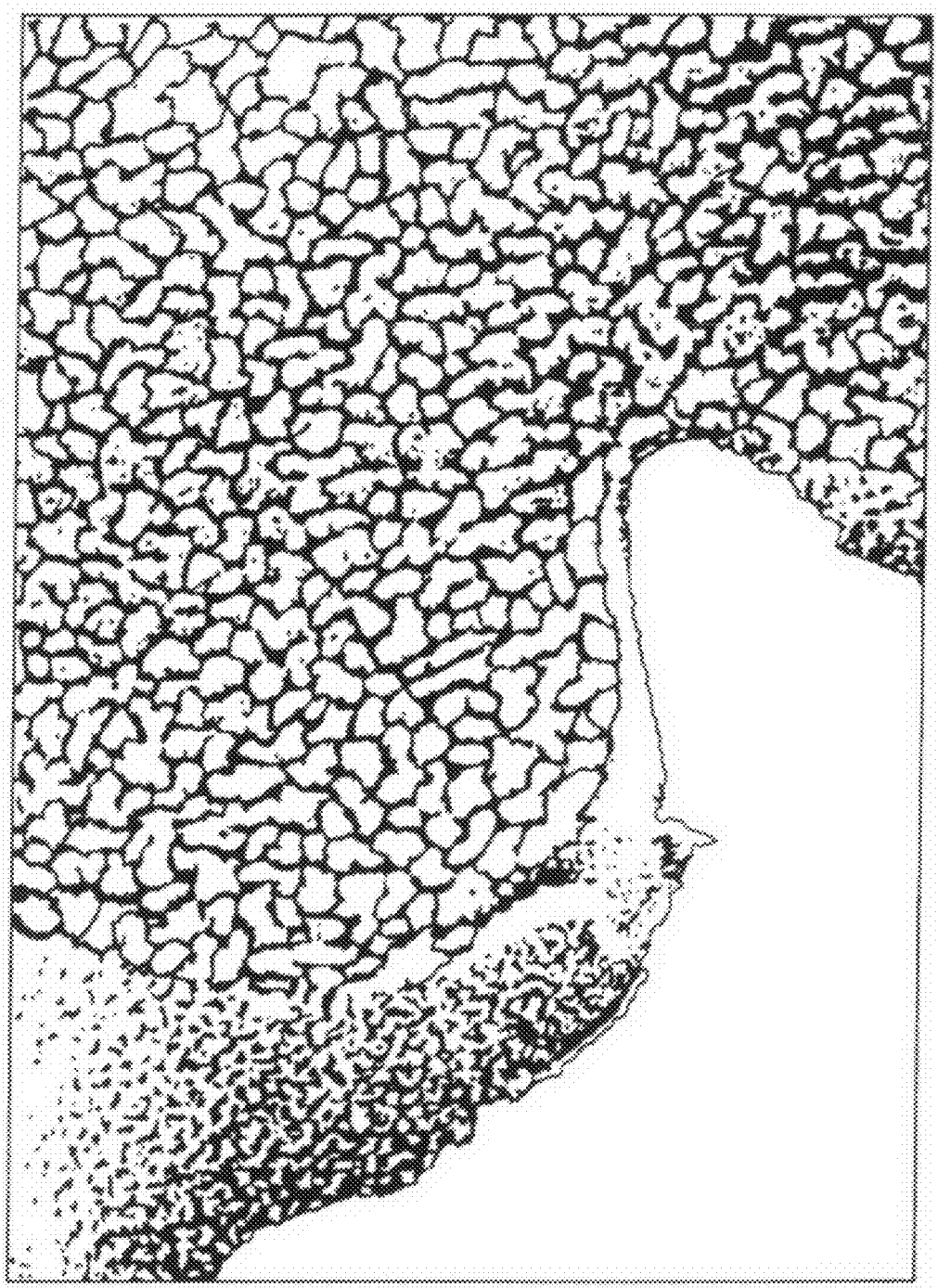
FIG. 2 is a picture of nano carbon particle structure under microscope at magnification of ×50,000.

The method of creating the present invention is illustrated in FIG. 1. Nano carbon particles of 80 nano meters and under are put into a heating chamber at 250 degrees Celsius for 30 minutes for purification and then cooled at room temperature. Said nano carbon particles are then mixed with large molecular massed plant based collagen. Ultrasound waves are then introduced to said mixture, shaking the nano carbon particles to rapidly break the collagen molecular structure until it is refined into collagen nanoparticulates and embedded within the 0.8 nano meter gaps of the nano carbon particles.

Figure 3:
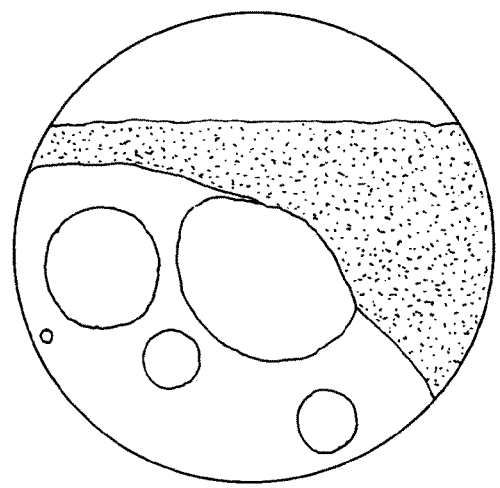
FIG. 3A-3D show series of pictures depicting the process of nano carbon particles refining collagen.
Figure 3:
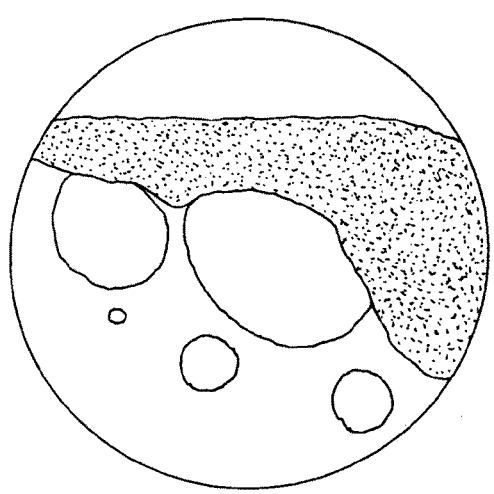
Figure 3:
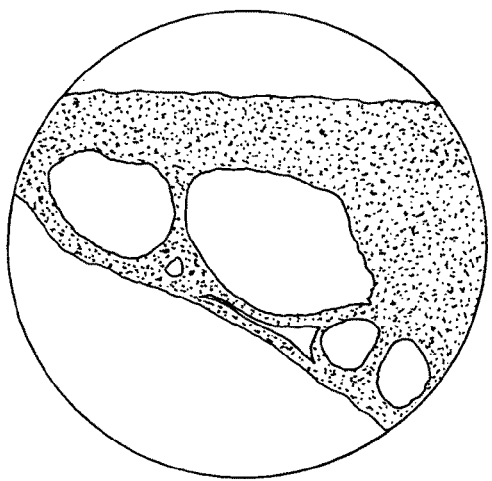
Figure 3:
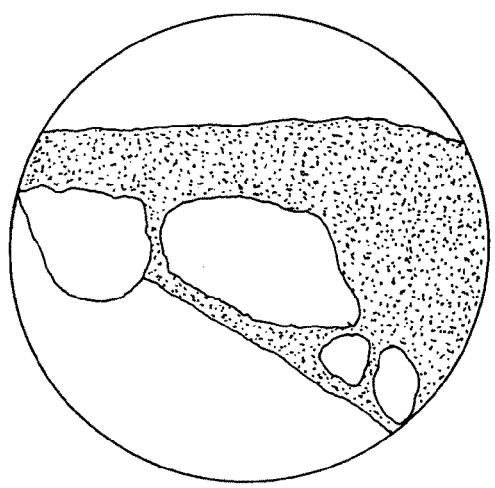

To understand the refinement process of collagen into nanoparticulates, an experiment I has been carried out as follows: Nano carbon particles are mixed with large molecular mass collagen and then two droops of said mixture are extracted and put between two glass slides. The mixture is observed under a microscope at a magnification of .times.1600, and photographed at intervals of 15 minutes. A total of four photos are taken and are presented at photos (A), (B), (C), and (D), as shown in FIG. 3. Of which photo (A) shows the nano carbon particles surrounding and absorbing the outer surface of the collagen, photos (B) and (C) show the collagen membrane being slowly broken apart by the nano carbon particles, and the collagen is being refined into smaller collagen particulates, which is then absorbed into and stored within the gaps of the nano carbon (D). Thus the creating of collagen nanoparticulates is completed.

From the above experiment, we can see that this method can effectively refine collagen of larger molecular mass. Said method creates nano collagen that can be easily absorbed by human skin to rejuvenate, restore firmness and elasticity. Thus the present invention proves the expected results and technical advancement above previous methods of collagen refinement.

I claim:

1. A method of using nano carbon to refine collagen into nanoparticulate collagen, comprising steps of:

preparing nano carbon particles of 80 nano meters;

putting said nano carbon particles into a heating chamber at 250 degrees Celsius for 30 minutes for purification and then cooling said nano carbon particles at room temperature;

mixing said nano carbon particles with plant based collagen to form a mixture;

applying ultrasound waves to said mixture; and shaking said nano carbon particles to break molecular structure of said plant based collagen until said plant based collagen being refined into collagen nanoparticulates and embedded within 0.8 nano meter gaps of said nano carbon particles.

* * * * *